(12) United States Patent
Molnar et al.

(10) Patent No.: US 11,247,046 B2
(45) Date of Patent: Feb. 15, 2022

(54) METHODS AND SYSTEMS FOR IMPLANTING A NEUROMODULATION SYSTEM AT A SURGICALLY OPEN SPINAL TREATMENT SITE

(71) Applicant: SynerFuse, Inc., Minneapolis, MN (US)

(72) Inventors: Gregory F. Molnar, Blaine, MN (US); Christopher G. Frank, New Brighton, MN (US); Justin D. Zenanko, Minnetrista, MN (US); Beth A. Lindborg, St. Paul, MN (US); Nazmi Peyman, Glen Allen, VA (US); Kyle Grube, Minneapolis, MN (US); Michael Park, Excelsior, MN (US); Matthew Hunt, Minneapolis, MN (US); Kathy Hill, St. Paul, MN (US)

(73) Assignee: SynerFuse, Inc., Minneapolis, MN (US)

( * ) Notice: Subject to any disclaimer, the term of this patent is extended or adjusted under 35 U.S.C. 154(b) by 181 days.

(21) Appl. No.: 16/519,512

(22) Filed: Jul. 23, 2019

(65) Prior Publication Data
US 2020/0030601 A1 Jan. 30, 2020

Related U.S. Application Data

(60) Provisional application No. 62/702,867, filed on Jul. 24, 2018.

(51) Int. Cl.
*A61B 17/70* (2006.01)
*A61N 1/05* (2006.01)
(Continued)

(52) U.S. Cl.
CPC ........ *A61N 1/0558* (2013.01); *A61B 17/7002* (2013.01); *A61B 17/7043* (2013.01);
(Continued)

(58) Field of Classification Search
CPC .............. A61N 1/0558; A61N 1/36062; A61N 1/37518; A61N 1/36071; A61N 1/36164;
(Continued)

(56) References Cited

U.S. PATENT DOCUMENTS

| 2009/0054951 A1 | 2/2009 | Leuthardt et al. |
| 2013/0310901 A1 | 11/2013 | Perryman et al. |

(Continued)

FOREIGN PATENT DOCUMENTS

| JP | 2007501675 | 2/2007 |
| JP | 2017507751 | 3/2017 |

OTHER PUBLICATIONS

International Preliminary Report on Patentability issued in related PCT/US2019/043136, dated Feb. 4, 2021.
(Continued)

*Primary Examiner* — Pedro Philogene
(74) *Attorney, Agent, or Firm* — Barnes & Thornburg LLP; Jeffrey R. Stone

(57) ABSTRACT

The present invention provides a single surgical method, procedure and/or system that creates open visual and physical access to an identified spinal treatment site that initially comprises spinal levels to be treated, wherein the spinal levels comprise at least one dorsal root ganglion. A spinal treatment procedure is performed generally in combination with implantation of a neuromodulation system that may comprise placement of electrical lead(s) on the at least one dorsal root ganglion, wherein each lead is in operative connection with a pulse generator that may also be implanted during the surgical method. Electrical stimulation may be generated with the pulse generator through the electrical leads to the at least one dorsal root ganglion during and/or after the closure of the identified spinal treatment site.

22 Claims, 16 Drawing Sheets

(51) Int. Cl.
  *A61N 1/36* (2006.01)
  *A61N 1/375* (2006.01)
  *A61B 17/56* (2006.01)
  *A61B 5/00* (2006.01)

(52) U.S. Cl.
  CPC ..... *A61N 1/36062* (2017.08); *A61N 1/36071* (2013.01); *A61N 1/37518* (2017.08); *A61B 5/4824* (2013.01); *A61B 17/7074* (2013.01); *A61B 2017/564* (2013.01)

(58) Field of Classification Search
  CPC ................ A61N 1/3787; A61N 1/0553; A61N 1/36182; A61N 1/36171; A61N 1/0551; A61N 1/06; A61N 1/36167; A61N 1/36157; A61N 1/37241; A61N 1/37247; A61N 1/36175; A61N 1/3616; A61N 1/37235; A61N 1/37264; A61N 1/36021; A61B 17/7002; A61B 17/7043; A61B 17/7074; A61B 2017/564
  See application file for complete search history.

(56) References Cited

U.S. PATENT DOCUMENTS

| | | |
|---|---|---|
| 2015/0165193 A1 | 6/2015 | Imran |
| 2016/0213917 A1* | 7/2016 | Dalm ................ A61N 1/36114 |
| 2016/0339251 A1* | 11/2016 | Kent .................... A61B 5/7235 |
| 2017/0196508 A1 | 7/2017 | Hunter |
| 2017/0312499 A1* | 11/2017 | Linker ................ A61N 1/0551 |
| 2018/0192943 A1 | 7/2018 | Annoni et al. |
| 2018/0317771 A1* | 11/2018 | Puryear .................... A61B 5/06 |
| 2019/0008386 A1* | 1/2019 | Puryear .................... A61N 1/08 |

OTHER PUBLICATIONS

International Search Report and Written Opinion issued in related PCT application No. PCT/US2019/43138, dated Oct. 15, 2019.
International Preliminary Report on Patentability issued in related PCT/US2019/043138, dated Feb. 4, 2021.
Extended European Search Report issued in EP 19808957, dated Feb. 8, 2021.

* cited by examiner

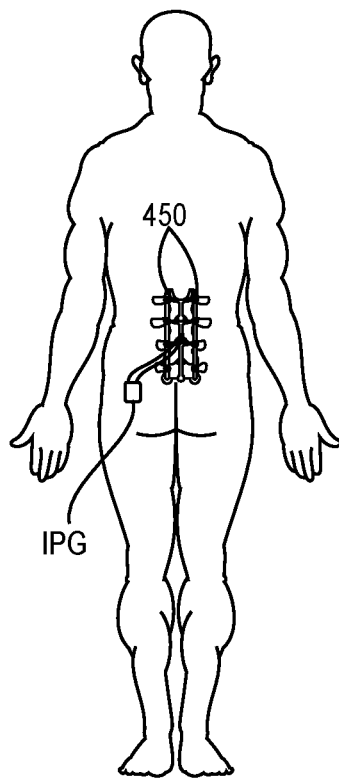 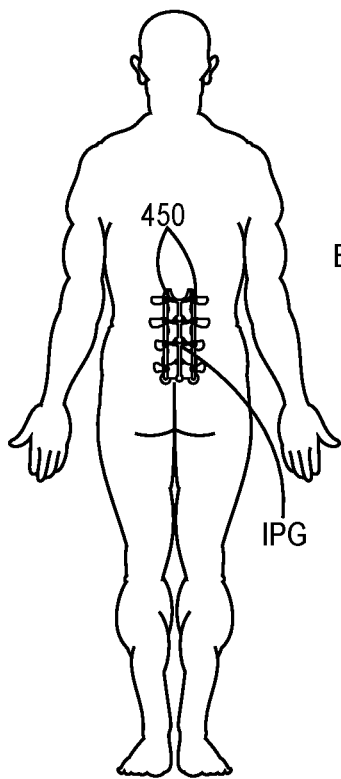 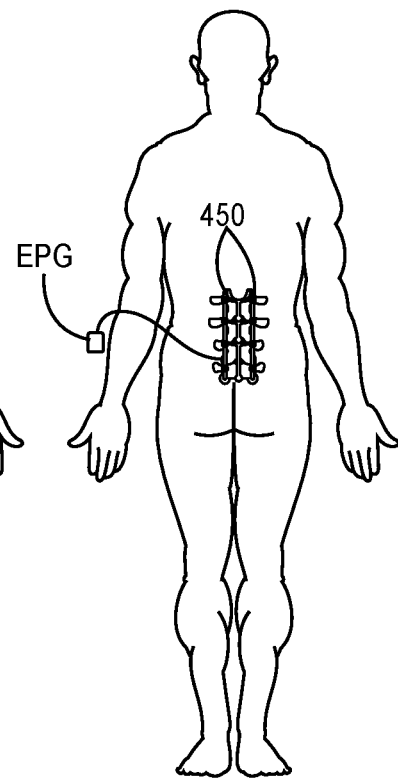
FIG. 11  FIG. 12  FIG. 13

METHODS AND SYSTEMS FOR IMPLANTING A NEUROMODULATION SYSTEM AT A SURGICALLY OPEN SPINAL TREATMENT SITE

CROSS-REFERENCE TO RELATED APPLICATIONS

This application claims the benefit of provisional application 62/702,867, filed Jul. 24, 2018 and entitled METHOD FOR IMPLANTING A NEUROMODULATION SYSTEM AT A SPINAL TREATMENT SITE, the contents of which are hereby incorporated by reference in their entirety.

STATEMENT REGARDING FEDERALLY SPONSORED RESEARCH OR DEVELOPMENT

Not Applicable

BACKGROUND OF THE INVENTION

Field of the Invention

The invention relates to a system and/or method for treating chronic spinal pain comprising a surgical procedure combining a spinal procedure such as vertebral fusion with implantation of a neuromodulation device, wherein the surgical procedure is conducted with open physical and visual access to the region of the spine undergoing treatment.

Description of the Related Art

Neuromodulation for the treatment of chronic spinal pain is a procedure that has been in use for decades. The procedure is generally prescribed to a patient only after they have gone through a spinal procedure that may involve vertebral fusion in an effort to mitigate and/or correct the supposed source of the pain. However, often such spinal procedures do not resolve the pain issues. After weeks, months and perhaps years of continued chronic pain and pain therapy through medications, including opioids, the patient may finally be prescribed neuromodulation for the treatment of chronic pain after failed back surgery.

The art does not provide single-surgical-procedure solutions that address these issues.

Accordingly, it would be highly advantageous to provide a surgical method and system that enables both a spinal procedure and neuromodulation system implantation within a single procedure.

It would be further highly advantageous to enable full physical and visual access to the associated spinal treatment site for placement of the surgical fusion device and the neuromodulation system.

It would be a further advantage to provide a surgical procedure that does not require advancement of an electrical lead through a patient's anatomy to reach the ultimate location of therapeutic efficacy.

It would be a further advantage to provide implantation of the neuromodulation system during the open spinal procedure, wherein the neuromodulation system may generate electrical stimulation during and/or after the surgical procedure.

It would be a further advantage to provide the implanted neuromodulation system as described above and for use in generating electrical stimulation only if the patient experiences pain after the surgical procedure.

Various embodiments of the present invention address these, inter alia, issues.

The figures and the detailed description which follow more particularly exemplify these and other embodiments of the invention.

BRIEF DESCRIPTION OF THE SEVERAL VIEWS OF THE DRAWINGS

FIG. 11 is a view of an embodiment of the present invention.

FIG. 12 is a view of an embodiment of the present invention.

FIG. 13 is a view of an embodiment of the present invention.

DETAILED DESCRIPTION OF THE INVENTION

Generally, various embodiments of the present invention are based upon the premise that many patients who suffer from chronic back pain, such as those who suffer for a long enough period of time or due to the severity of their particular condition, are also separately suffering from neuropathic pain that cannot be corrected by spinal surgery. In such a case it is a misnomer to say that a patient is suffering from "failed back surgery" but more accurately that the back surgery simply does not address the neuropathic pain that may have been in place prior to the back surgery.

The present invention provides a method for combining the implantation of a spinal treatment device with the implantation of a neuromodulation device, or at least a neuromodulation lead of a neuromodulation device, into a single combination procedure performed at the spinal treatment site. The present invention thus provides the potential to treat both back stabilization issues and neuropathic pain issues in a single procedure, with the additional benefit of minimizing the amount of pain medications, including opioids and other pain medications, that a patient may otherwise require to manage chronic back pain.

Figure 1A:
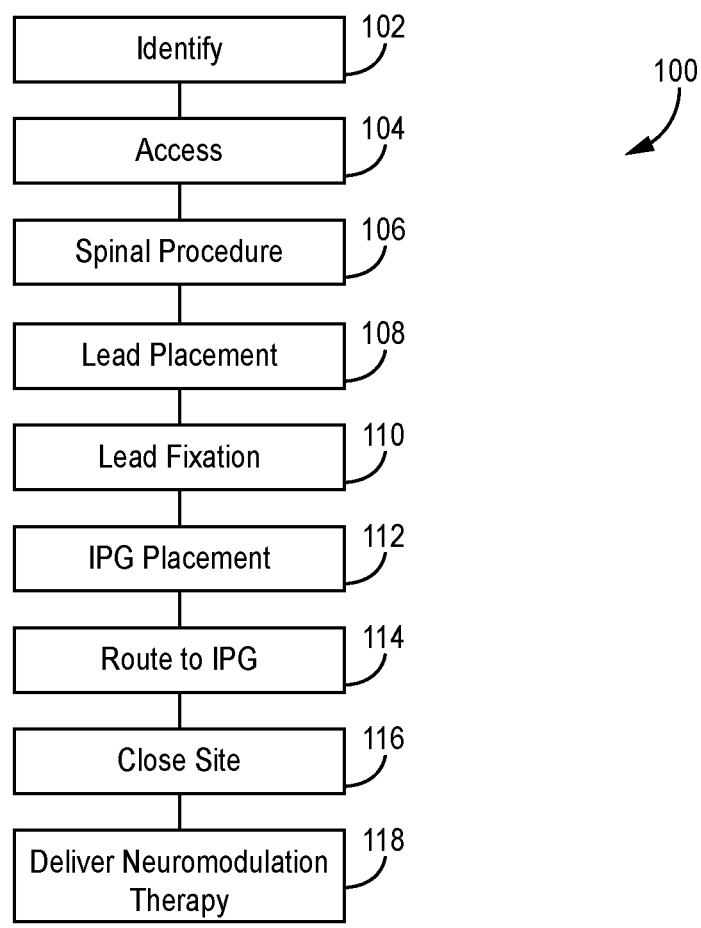
FIG. 1A is a block diagram of an embodiment of the present invention.

FIG. 1A is a block diagram of one embodiment of a combination spinal procedure and neuromodulation procedure (100) wherein neuromodulation therapy is delivered after completion of the combination procedure.

Initially, the spinal treatment site is identified (102) including the vertebral and spinal levels that are to be treated in the combination procedure (100). The target vertebral levels are the vertebral levels identified for spinal treatment procedure. The target spinal levels are the spinal levels identified for the spinal treatment procedure. The target spinal levels may correspond with the target vertebral levels or be one to two levels above or below the target vertebral levels. The target spinal levels comprise one or more dorsal root ganglia and may include one or both dorsal root ganglion in bilateral relationship to each other, or may include only a single unilateral dorsal root ganglia at a specific identified spinal level. Additionally, or separately, the target spinal levels may be unilateral and may include only a single or multiple spinal levels in a chained relationship on a single side of the spinal cord.

The method for identifying the target spinal levels is performed using known techniques that may comprise a mapping of the dermatome procedure performed by a medical professional on a patient that has been identified to receive a spinal treatment. A result of the mapping of the dermatome is the identification of the specific dorsal root ganglia that comprise the target spinal level or target spinal levels. In accordance with the present invention the target spinal levels more specifically will include the corresponding dorsal root ganglia at each of the targeted spinal levels and whether the target spinal level includes a bilateral or unilateral treatment of the dorsal root ganglia at each of the target spinal levels identified.

The target treatment site comprises the target spinal levels and corresponding dorsal root ganglia, unilateral or bilateral, that have been identified by the above procedure. The target treatment site further may further include the target identified vertebral levels for the spinal procedure.

Following identification (102) the spinal treatment site is accessed (104) through one or more incisions at or near the spinal treatment site. In an open retrograde spinal procedure the incision will enable visual access to all or of portion of the target vertebral level or levels and the target spinal level or levels.

Thus, "routing" and "placing", as used herein in terms of routing and placing the leads and electrodes, and placing the IPG, are defined as laying directly on, or positioning directly on or at, the relevant anatomical location with full visualization and physical access and without initial epidural access or other internal non-visualized advancement from an access point to the relevant anatomical location. Routing and placing as used and defined herein is as a result of the opening created by the "open access" which is defined herein as an open surgical site, by surgical incision or other means, that allows full visual and physical access of the spinal treatment site to enable the defined routing and placing. "Open access" specifically does not include traditional epidural access, or any similarly non-open access, which requires, inter alia, epidural advancement and/or tunneling to route and place the leads, electrodes and/or IPG.

The spinal procedure is performed (106) by implanting a spinal stabilization device that may comprise a pair of bilaterally spaced rods each of the rods affixed to the target vertebrae using at least a pair of pedicle screws to secure each rod to a target vertebrae. A transverse bar or plate may extend across the spaced rods to provide further spinal stabilization via the spinal fixation device.

In combination with the spinal procedure at the treatment site, a neuromodulation implantation procedure is also performed at the treatment site. The neurmodulation implantation procedure includes the placement of one or more neurostimulation leads at the target spinal levels, and more specifically, at the dorsal root ganglia that comprise the target spinal levels (108).

The neurostimulation leads may comprise a distal portion having one or more electrodes positioned at the distal portion. The neurostimulation lead(s) may further comprise a proximal portion capable of coupling to an implantable pulse generator. The neurostimulation lead(s) may further comprise one or more electrically conductive wires capable of receiving an electrical signal in a distal portion, when electrically coupled to a pulse generator. The neurostimulation lead(s), when coupled to an implantable pulse generator, are then capable of delivering an electrical signal via the electrode(s) to a target site, such as a target dorsal root ganglia, when the electrode(s) are placed in therapeutic proximity thereto.

The procedure for placing of the neurostimulation leads may include placing the distal segment of one or more neurostimulation leads at the corresponding one or more target dorsal root ganglia such that the one or more electrodes of a neurostimulation lead is in therapeutic proximity to the target dorsal root ganglia. Accordingly, when the neurostimulation lead is coupled to an implantable pulse generator and an electrical signal is delivered to the target dorsal root ganglia via the neurostimulation, the delivered electrical signal results in neuromodulation of the target dorsal root ganglia.

The neurostimulation lead(s) may be fixated (110) in therapeutic proximity to the corresponding target dorsal root ganglia by a variety of methods. The neurostimulation leads may be anchored using a suture at a distal portion thereof, the neurostimulation leads may be anchored by suturing a portion of the neurostimulation lead to a vertebral bone or to a portion of the spinal fixation device. Alternatively, the neurostimulation lead(s) may be anchored in place via coupling to an implantable pulse generator (IPG) in a position that provides strain relief and that otherwise minimizes lead displacement forces.

The implantable pulse generator may be placed/implanted (112) during the spinal procedure in an anatomical location that is dependent upon the particular treatment procedure performed or dependent upon physician preference or dependent upon patient preference or some combination thereof.

The neuromodulation procedure may further comprise routing of the proximal portion of the neurostimulation lead to an implantable pulse generator (114), with operative electrical connection between the lead(s) and the implantable pulse generator. In the situation where the spinal process bone at the treatment site is removed, the implantable pulse generator may be positioned in the carved out portion of the treatment site at the vertebral level where the bone has been removed. The proximal portion of the one or more neurostimulation leads may then be routed to the implantable pulse generator positioned at the treatment site.

Once the implantable pulse generator has been placed and coupled to the proximal segment of the neurostimulation leads the one or more incisions at the spinal treatment site may be closed (116) such as via suture or any other suitable means.

The implantable pulse generator may then be activated to deliver, via the one or more neurostimulation leads, a neuromodulation therapy comprising electrical stimuli to one or more of the targeted dorsal root ganglia.

In all described embodiments herein, the neuromodulation therapy may be delivered during the surgical procedure, i.e., when the spinal treatment site incisions remain open and/or after closure of the spinal treatment site. In some embodiments, the neuromodulation therapy may be delivered or initiated immediately upon closure of the spinal treatment site or may be delayed a predetermined period of time. In other embodiments, the neuromodulation therapy may be delivered or initiated only if and when the patient experiences back pain after completion of the combined surgical procedure.

Figure 1B:
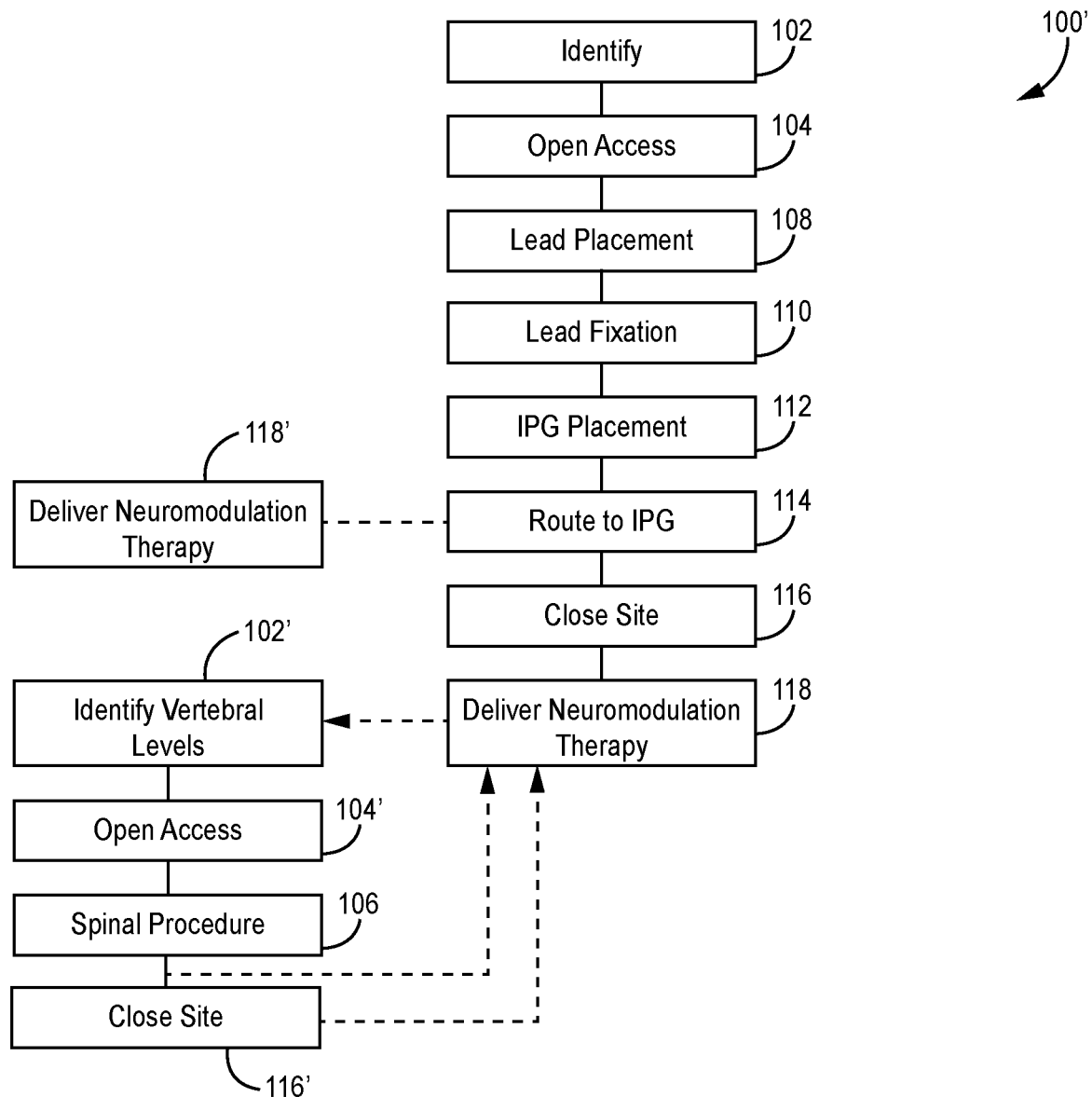
FIG. 1B is a block diagram of an embodiment of the present invention.

FIG. 1B provides a block diagram of an embodiment of a procedure 100' comprising an open visual and physical access to the surgical site as described above. However, in this case, the neuromodulation system is placed and implanted and the access site closed without, at least initially, performing the spinal procedure (106). In this embodiment, the benefit of an open visual access site to route leads and place electrode(s) is significant to allow the surgeon to ensure proper routing and maximize therapeutic efficacy of the neuromodulation stimulation therapy by, inter alia, proper placement of the electrode(s) in therapeutic proximity with the target dorsal root ganglion/ganglia. Following completion of this procedure, if the patient requires the spinal procedure (106) may be performed, with placement of the relevant fixation rods over or under the previously placed leads as is shown herein in further detail in FIGS. 5-16.

Thus, the spinal level(s), including target dorsal root ganglion/ganglia (DRG(s)) for lead routing and electrode(s) placement are identified at (102). As with FIG. 1A, targeted dorsal root ganglion/ganglia may be bilateral at a single, or more than one, spinal level, or may be unilateral at a single, or more than one, spinal level. The identifying step (102) is similar in other respects to FIG. 1A.

After identifying the spinal level(s) and targeted DRG(s), the spinal treatment site is opened for full visual and physical access to the identified spinal level(s) (104). As discussed, this open visual and physical access is highly advantageous, ensuring optimal placement and performance of the placed and implanted system. Next, at least one lead is placed within the open spinal treatment site (108). Note that because the access site is fully open to visual and physical access, there is no need to "advance" leads through the patient's anatomy. Instead, the surgeon may physically lay or place the lead(s) in the desired position. Lead(s) comprise a proximal end for operative electrical connection with a pulse generator and a distal end comprising at least one electrode for delivering an electrical signal to the target DRG. The pulse generator generates an electrical signal that is conducted along the lead and to the distal placed electrode(s) which then transmit the electrical signal to the target DRG. Leads are fixed 110 as described above in FIG. 1A.

The pulse generator, most typically an implanted pulse generator (IPG) is then placed using the advantages provided by the full visual and physical access of the opened spinal treatment site at 112. The placed lead(s) are routed to the IPG, wherein the proximal ends of the lead(s) are operatively electrically connected thereto (114) and the access site may then be closed at 116. Note that in some embodiments, the IPG may be placed generally along the midline of the spinal column and may be located anatomically below the location of the placed electrode(s). This configuration will generally result in the lead(s) being routed along, but not across, the spinal column and midline thereof. In other embodiments, the IPG may be placed to one side of the spinal column, resulting in some cases in at least some lead(s) routed across the spinal column and midline thereof.

In one embodiment, neuromodulation stimulation therapy at the identified spinal level(s) and to the targeted DRG(s) may be delivered post-closure of the access site 118. In an alternate embodiment, neuromodulation stimulation therapy may also be delivered at the identified spinal level(s) and to the targeted DRG(s) before closure of the access site to help mitigate any pain resulting from the procedure itself. This pre-closure neuromodulation delivery step is shown as 118' and with dashed lines as it is an optional alternative embodiment step.

Initially, it is contemplated in this embodiment that a spinal procedure such as vertebral stabilization or fusion is not indicated. However, after the access site is closed at 106 and after delivery of neuromodulation therapy at 118, the patient may develop a need for vertebral stabilization, e.g., fusion. In that case, as shown in dashed lines and as discussed above, identification of the vertebral levels to be treated is completed at 102' with subsequent open visual and physical access to the spinal treatment site at 104'. Next, the surgical procedure is executed at 106 which may comprise, as is described infra, securement of bilaterally spaced fixation rods across the identified vertebral levels and with an optional spanning rod therebetween. Fixation rods may be secured to the identified vertebra with pedicle screws as is well known in the art.

The placement of the fixation rods and optional spanning rod relative to the previously placed IPG and leads may then be executed as discussed below in relation to FIGS. 5-16. In some cases, the fixation rods and/or optional spanning rod may be placed over the previously placed leads and the IPG may be disposed below the location of the related electrode(s). In other cases, the fixation rods and/or optional spanning rods may be placed under the previously placed leads. In some cases, the previously placed IPG may be moved from the original placement and moved in accordance with the embodiments discussed below, including but not limited to those embodiments that secure the IPG to one or both of the fixation rods and/or to the spanning rod when present.

Figure 2A:
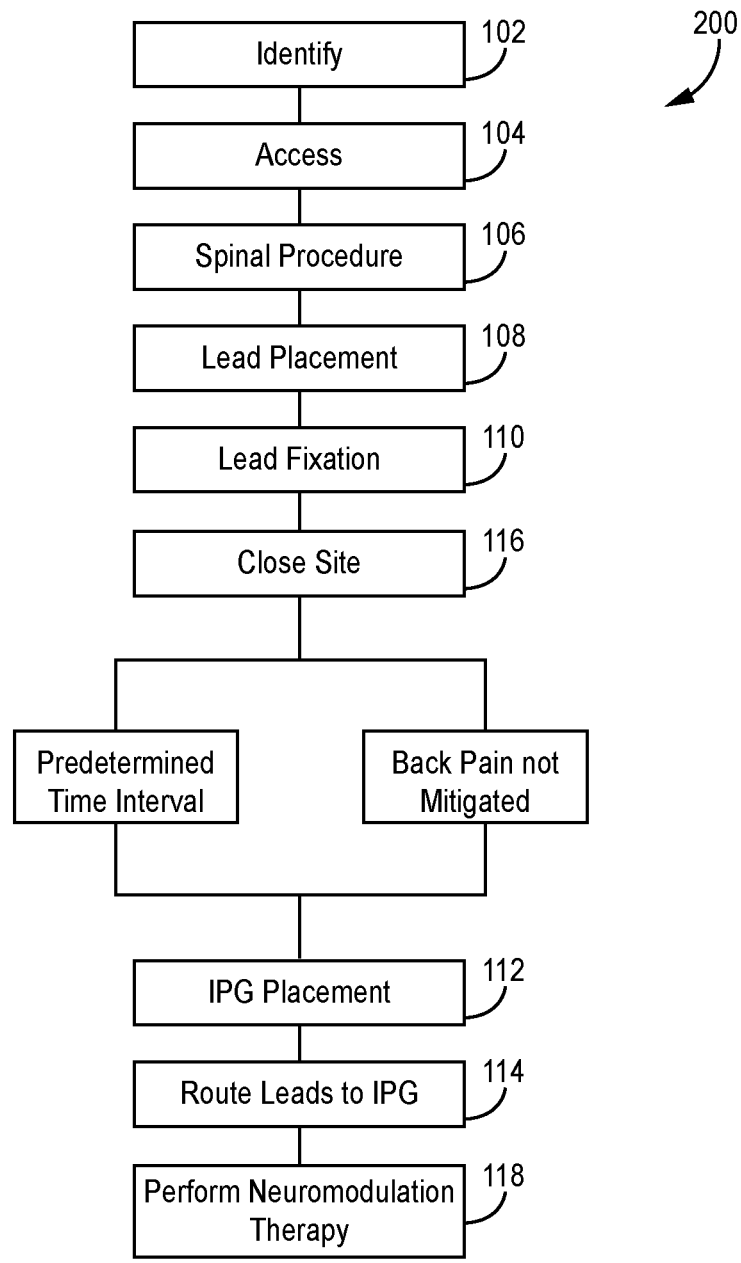
FIG. 2A is a block diagram of an embodiment of the present invention.

FIG. 2A is a block diagram of another embodiment of a combination spinal procedure and neuromodulation procedure identical to the procedure of FIG. 1, except that in the procedure of FIG. 2A the lead(s) are routed to the implantable pulse generator after the completion of the combination spinal procedure and neuromodulation procedure. In this embodiment of the present invention, the neuromodulation procedure includes placement of the one or more neurostimulation leads (108) prior to completion of the spinal procedure but may, or may not, include placement of the implantable pulse generator (112) or routing and operative coupling of the neurostimulation leads to the pulse generator (114) prior to completion of the spinal surgery and closure of the site (116).

In such an embodiment, a patient may be implanted with the one or more neurostimulation leads at the corresponding one or more target dorsal root ganglia but the delivery of neuromodulation therapy may be delayed until a predetermined period of time after completion of the surgical procedure and/or until or if the patient experiences back pain after the surgical procedure is completed, such predetermined period of time may include allowing a patient to recover from the spinal fixation implant procedure and to determine if the patient needs neuromodulation therapy or if the spinal fixation implant has sufficiently removed the patient's need for pain therapy.

Thus, FIG. 2A comprises a combined spinal implant and neuromodulation implant procedure 200 with the identification (102), access (104), spinal procedure (106), lead placement (108), lead fixation (110) and site closure (116) steps in the same order and as described above in connection with FIG. 1. Placement of the IPG (112) and routing and operative electrical connection of the proximal portion of the lead(s) to the IPG (114) are also as described as above in FIG. 2.

FIG. 2A, however, may delay placement of the implantable pulse generator (112), routing and operative electrical connection of the proximal portion of the lead(s) to an implantable pulse generator (IPG) (114), and delivery or performance of neuromodulation therapy (118) to a point after site closure (116). As discussed above, the placement of the IPG (112) with lead routing and operative connection thereto (114) and delivery of neuromodulation therapy (118) may be delayed for a predetermined time following site closure (116). Alternatively, IPG placement (112) with lead routing and operative connection thereto (114) and delivery of neuromodulation therapy (118) may be delayed to determine if the patient's back pain has not been sufficiently mitigated or treated. In each of these cases, the IPG will be connected with previously placed and fixated lead(s) upon the passage of the predetermined time interval and/or indication that the patient's back pain was not sufficiently treated with the spinal procedure, e.g., vertebral fusion.

Indeed, in one embodiment of FIG. 2A, it is possible that no IPG placement (112) will be required if, e.g., the patient's back pain is sufficiently treated with the steps 102-116 of FIG. 2. This is the outcome if the only parameter for continuing the method to implant the IPG with routing and connection of the previously placed and fixated lead(s) thereto with subsequent initiation and delivery of neuromodulation therapy (112-118) is whether or not the patient's back pain is sufficiently treated or mitigated.

Figure 2B:
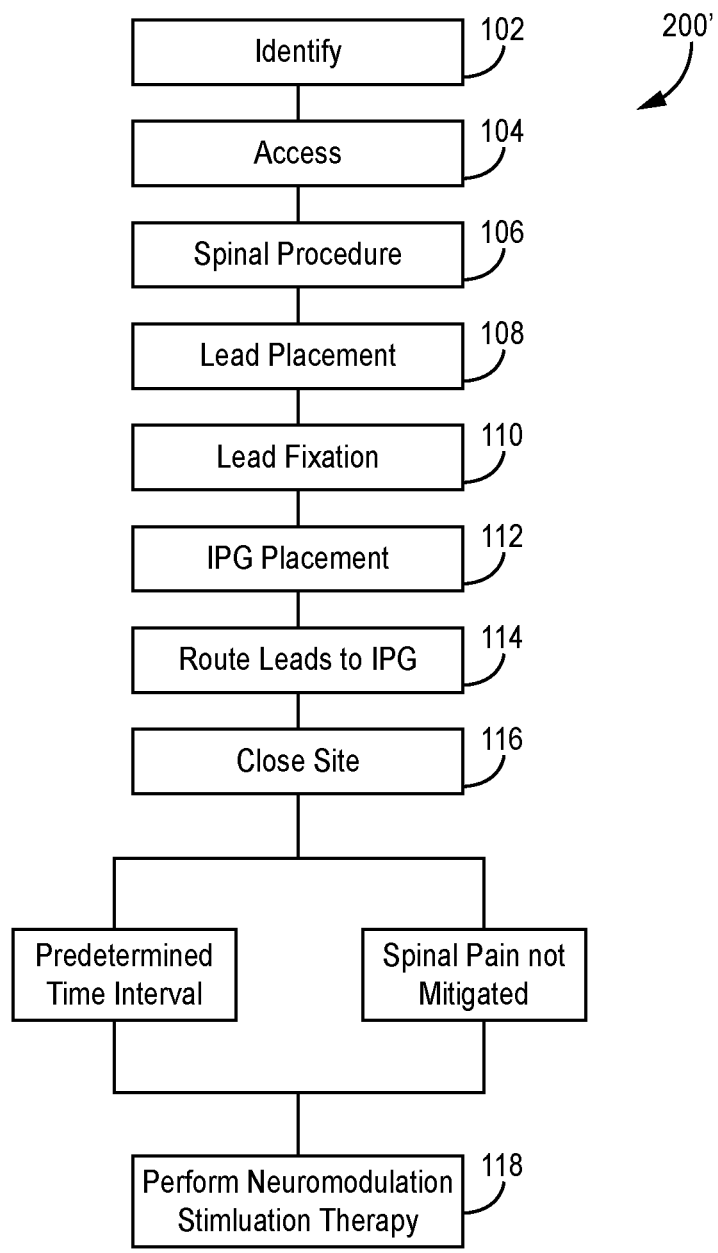
FIG. 2B is a block diagram of an embodiment of the present invention.

FIG. 2B method process 200' is similar to FIG. 2A, except that in FIG. 2B, the IPG is placed (112) and leads are routed to the IPG (114) before closing the access site (116). Then, as shown, a predetermined time interval may pass before initiating neuromodulation stimulation therapy (118). Alternatively, the patient's pain levels may be monitored post access closure and if not sufficiently mitigated, then neuromodulation stimulation therapy may be initiated.

Figure 3:
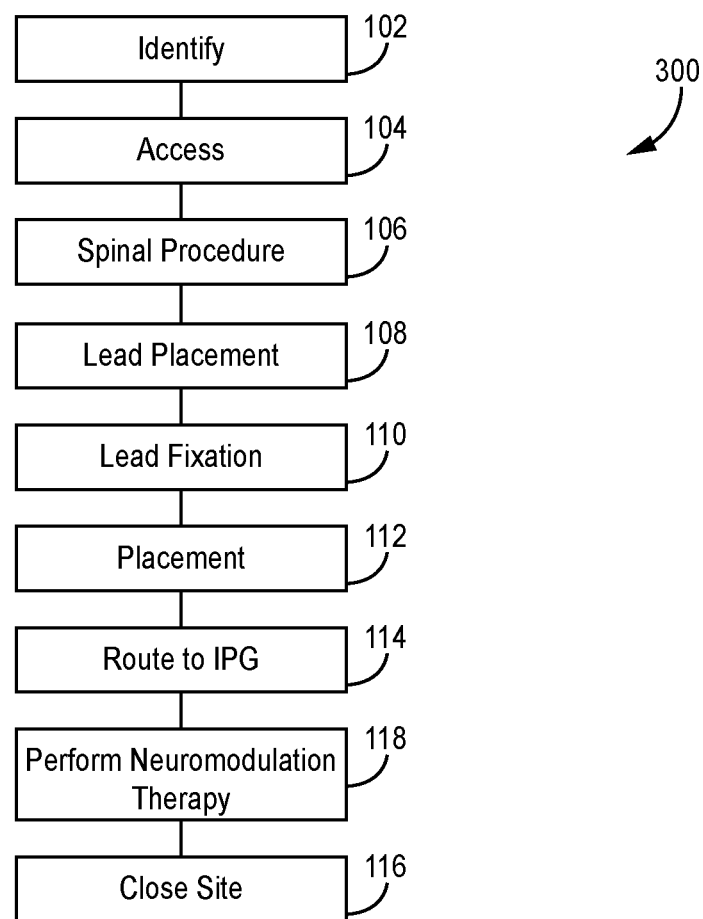
FIG. 3 is a block diagram of an embodiment of the present invention.

FIG. 3 is a block diagram of an alternative embodiment of a combination spinal procedure and neuromodulation procedure 300 wherein a neuromodulation therapy is delivered prior to completion of the spinal procedure. In this embodiment of the present invention, a patient may being receiving neuromodulation therapy prior to completion of the spinal procedure. In such an embodiment, the implantable pulse generator is coupled to the neuromodulation lead and a neuromodulation therapy is provided prior to closure of the one or more incisions made during the spinal procedure. In such an embodiment, the neuromodulation therapy may be provided in order to reduce or remove acute pain resulting from the spinal procedure as well as reduce, remove, remediate or minimize chronic pain after completion of the spinal procedure and/or after recovery from the spinal procedure.

Thus, procedure 300 is similar to FIG. 1 as it employs the same steps as described in connection with FIG. 1 and in the same order as follows: identification (102); access (104); spinal procedure (106); lead(s) placement (108); lead(s) fixation (110); placement of the IPG (112); routing of the lead(s) and operative electrical connection of the proximal portion of the lead(s) to the placed IPG (114). However, instead of closing the site then performing neuromodulation therapy as in FIG. 1, procedure embodiment (300) reverses these steps as follows: After step (114), neuromodulation therapy is performed (118), then the surgical site is closed (116).

As discussed above, the embodiment of FIG. 3 may be provided in order to reduce or remove acute pain resulting from the spinal procedure (106) as well as reduce, remove, remediate or minimize chronic pain after completion of the spinal procedure (106) and/or after recovery from the spinal procedure (106).

In each of the above-described procedures, methods or systems, the placement of the lead(s) (108) is achieved by therapeutic proximity to a target dorsal root ganglion. Here, the term therapeutic proximity is defined as the relationship between the lead(s) and/or electrode(s) of the lead(s) and the target dorsal root ganglion such that a therapeutic electrical signal may be conducted between the lead(s) and/or electrode(s) and the target dorsal root ganglion. In some cases therefore, therapeutic proximity will be achieved by placing the lead(s) and/or electrode(s) in physical contact with the target dorsal root ganglion, wherein the lead(s) and/or electrode(s) may, or may not be, implanted within the target dorsal root ganglion. A preferred embodiment comprises a non-implanted physical contacting placement of the lead(s) and/or electrode(s) with the target dorsal root ganglion. Alternatively, no physical contact will be required between the lead(s) and the target dorsal root ganglion to achieve the required conduction of electrical stimulation signals between the lead(s) and/or electrode(s) and the target dorsal root ganglion.

Figure 4:
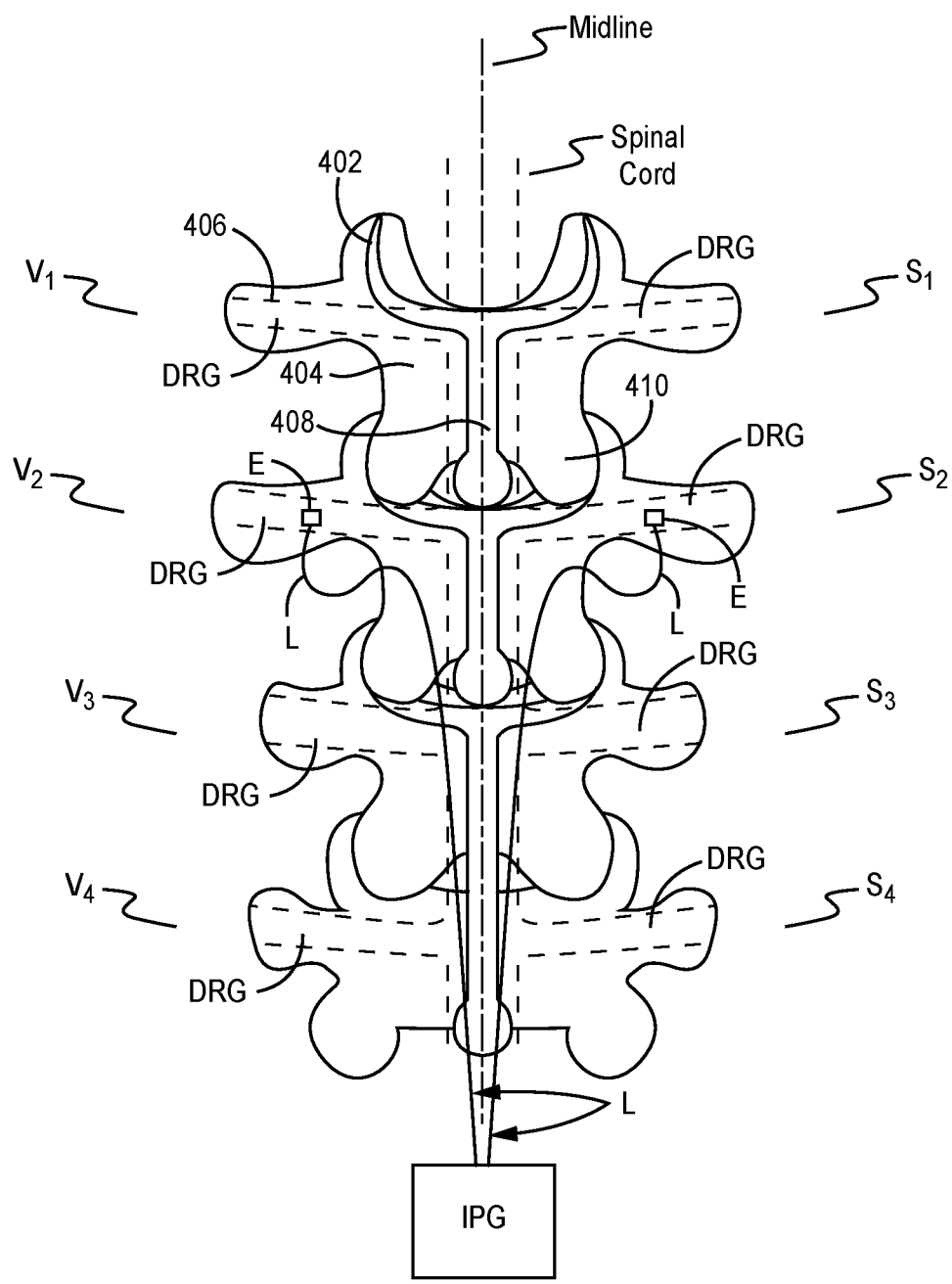
FIG. 4 is a view of an embodiment of the present invention.

Turning now to FIG. 4, a set of neurostimulation leads L is shown in therapeutic contact with a corresponding set of dorsal root ganglion at a single target identified spinal level $S_2$ with a bilateral placement of the neurostimulation leads L each in therapeutic proximity to a corresponding dorsal root ganglion (DRG) target.

Anatomically, FIG. 4 illustrates four vertebrae (V) each vertebra (V) comprising two superior articular processes (402), a vertebral body (404) with two transverse processes (406) a spinous process (408) and two inferior articular processes (410). The superior articular processes (402) are generally shaped to be complementary to and articulating within the inferior articular processes (410). The spinal cord is shown in dashed lines as it traverses through each vertebra (V). A dorsal root ganglion (DRG) (also shown in dashed lines) branches away from the spinal cord, wherein two dorsal root ganglia (DRG) extend bilaterally, i.e., in substantially a transverse direction, away from the spinal cord on either side of the spinal cord and the midline of the spinal cord as shown. Thus, there are two dorsal root ganglia (DRG) associated with each vertebra (V).

Identification of vertebral levels as discussed above in connection with FIGS. 1-3 may comprise two or more than two vertebra (V) for purposes of executing the spinal procedure, e.g., vertebral fusion procedure. The skilled artisan will readily understand that the set of 4 vertebrae V shown in FIG. 4 are merely illustrative and that more, or fewer, than 4 vertebrae V may be involved in the various embodiments of the present invention.

Identification of spinal levels as discussed in connection with FIGS. 1-3 for purposes of executing the placement of the lead(s) L, may comprise one or both DRG's associated with one vertebra (V), for example an identified spinal level of $S_1$, $S_2$, $S_3$, or $S_4$ as those spinal levels are shown in FIG. 4. Alternatively, the identified spinal levels may comprise one or two DRG's associated with more than one vertebra (V), e.g., $S_1$, $S_2$, $S_3$, and/or $S_4$. The identified spinal level(s) may be coincident with, overlapping or offset from, the identified vertebral levels and/or may located at a vertebra (V) that is not part of the identified vertebral level(s) V, e.g., $V_1$, $V_2$, $V_3$, and/or $V_4$ also shown in FIG. 4.

Typically, the identified vertebral levels may comprise vertebrae (V) that are adjacent to or connected with each other. Thus, a typical identified vertebral level may comprise exemplary vertebral levels $V_1$ and $V_2$, which are the subject of the spinal procedure, e.g., stabilization and/or fusion of vertebrae (V) at the exemplary identified vertebral levels $V_1$ and $V_2$.

The identified spinal levels $S_1$, $S_2$, $S_3$, and/or $S_4$ may comprise or involve one, or more than one, vertebra V.

In FIG. 4, there is no spinal procedure device shown, only a neuromodulation device or system. Thus, as shown, and in conformance with the discussion above in connection with FIGS. 1-3, the identified spinal level is located at $V_2$. Further, a neuromodulation device or system comprising an IPG that is placed with two electrical leads (L) in operative electrical connection therewith. The electrical leads (L) are routed along either side of the spinal column to the identified spinal level, therefore each lead (L) does not cross the midline of the spinal column. At least one electrode (E) is located at the distal end of each electrical lead and is located within therapeutic proximity of the subject DRG. As also discussed above, FIG. 4 is the result of an open-access surgical incision that exposes the subject portion of the spinal column, providing the surgeon with physical and visual access to the relevant vertebrae (V).

Figure 9A:
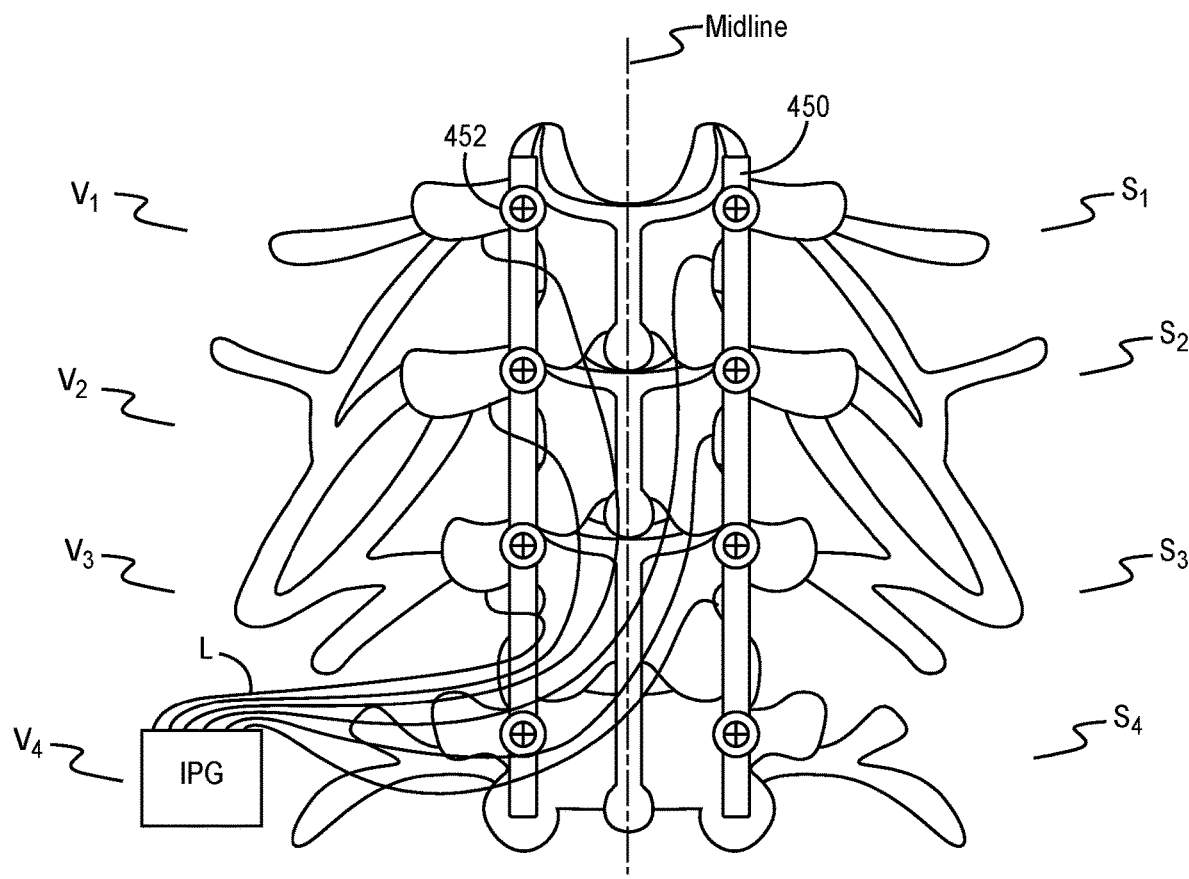
FIG. 9A is a view of an embodiment of the present invention.

As is further shown, the IPG is placed effectively below the placed leads L which facilitates the illustrated routing of the leads (L) along the midline of the spinal column. Placement of the IPG in all cases discussed herein may be below or above the placed leads L. In addition, the IPG may be placed along the midline of the spinal column as illustrated or may be placed off to one side of the midline of the spinal column as best seen in FIG. 9A which further illustrates at least some of the lead(s) L crossing the midline of the spinal column when they are routed and the electrodes E placed in therapeutic proximity with the targeted DRG.

Figure 5:
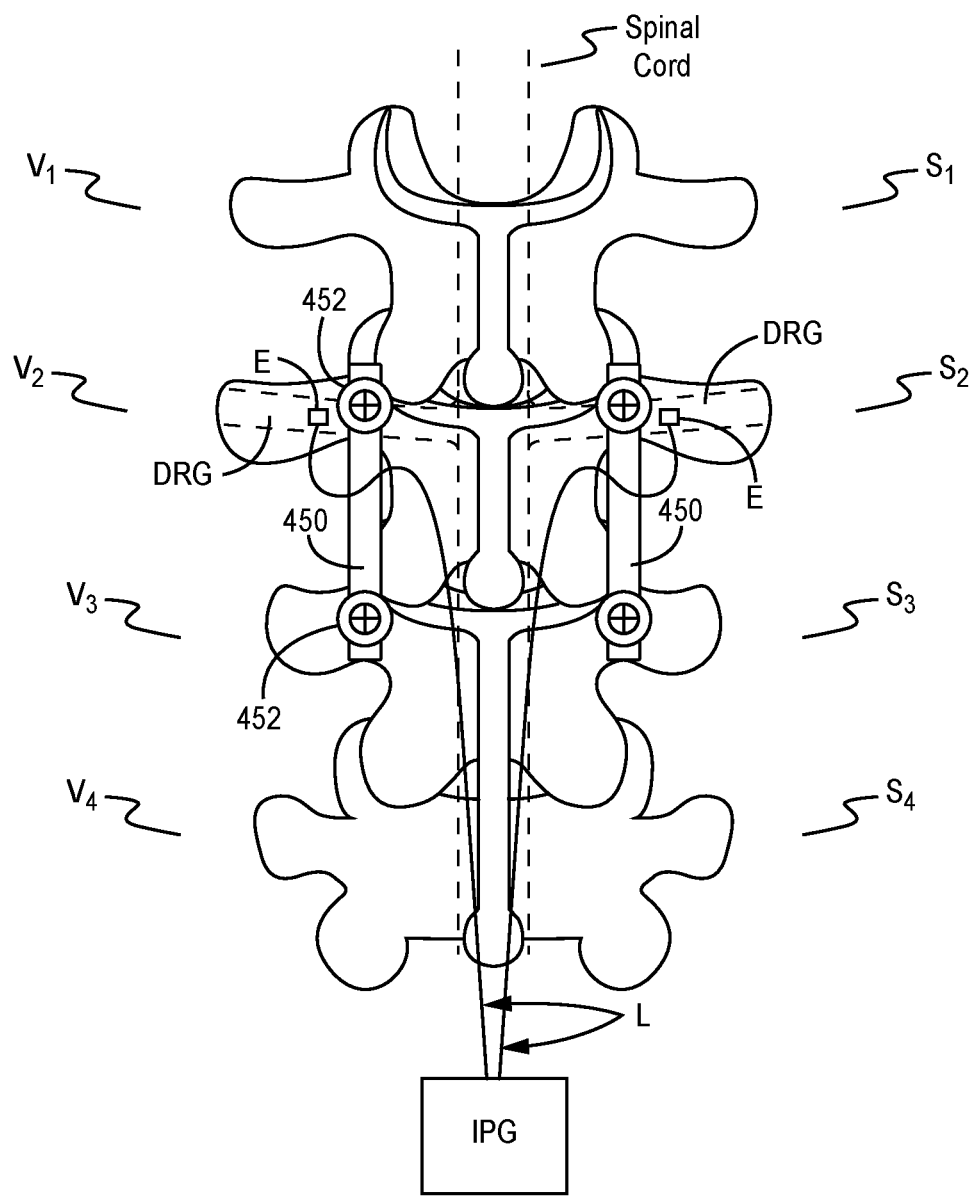
FIG. 5 is a view of an embodiment of the present invention.

FIG. 5 is an illustration of a spinal treatment site including two spinal fixation rods (450), fixed in place on either side of the midline with pedicle screws (452) at opposing ends of the fixation rods (450) as is known in the art, wherein the fixation rods (450) are affixed between the identified vertebral levels $V_2$ and $V_3$, thereby effectively fusing the two associated vertebrae (V) together. The neurostimulation leads L and related electrode(s) E are in routed and placed therapeutic proximity to the DRG's located at the identified target spinal level $S_2$. In this case, the identified target spinal level $S_2$ is located at a vertebra (V) that is also within the identified target vertebral levels $V_2$ and $V_3$. The IPG is shown as placed at a location that is below the routed and placed leads L and electrodes E. FIG. 5 is also achieved using an open-access surgical incision that exposes the subject portion of the spinal column, providing the surgeon with physical and visual access to the relevant vertebrae (V).

Figure 6:
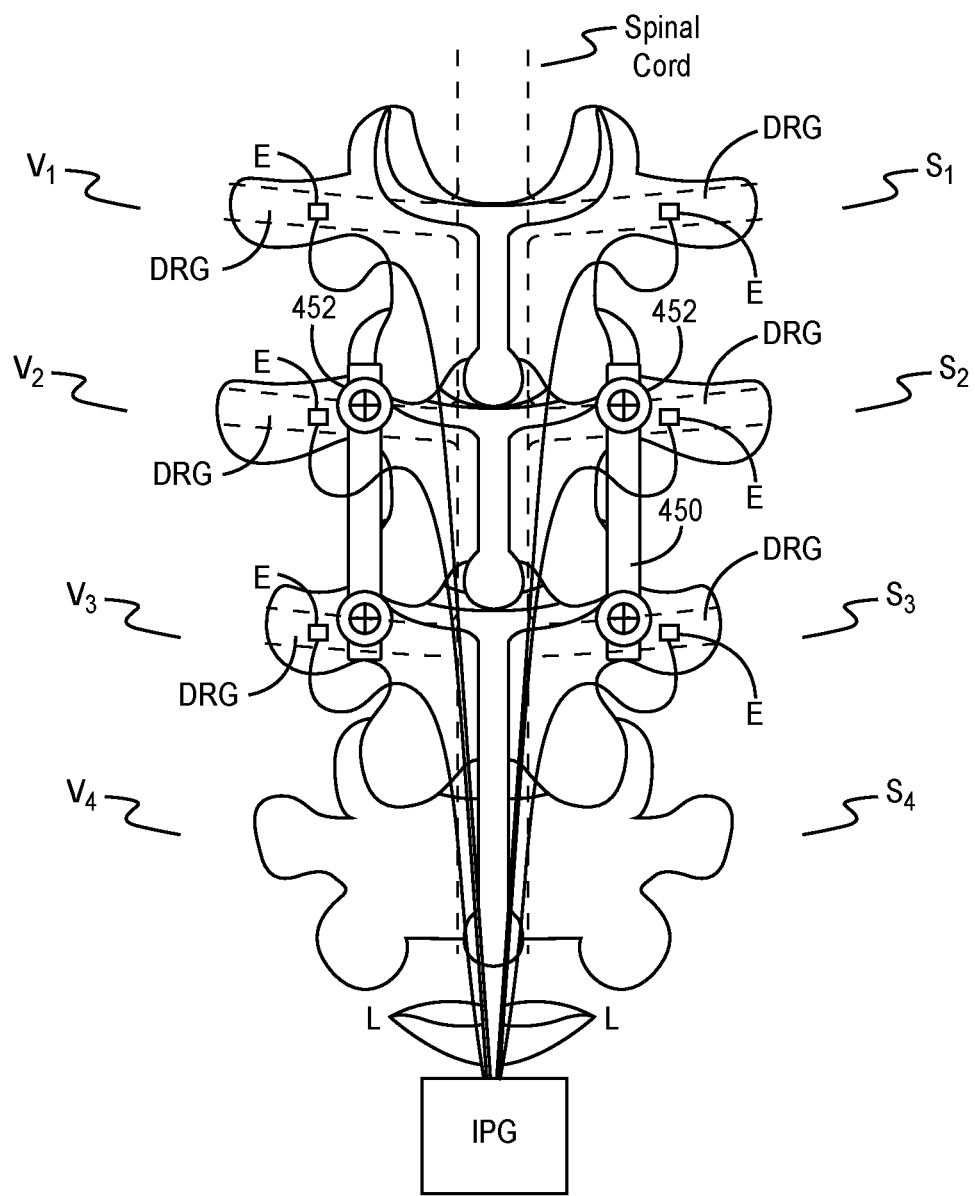
FIG. 6 is a view of an embodiment of the present invention.

FIG. 6 is an illustration of a spinal treatment site similar to that of FIG. 5, including a spinal fixation device and neuromodulation device, with the identified vertebral levels shown as $V_2$ and $V_3$. However, in this case one of the identified spinal levels does not involve the vertebrae (V) within the identified vertebral levels. Instead, the identified spinal levels are shown as $S_1$, $S_2$ and $S_3$, wherein $S_1$ is outside of (above) the identified vertebral levels $V_2$ and $V_3$. Accordingly, the leads L and related electrode(s) E are shown as placed one spinal level above at $S_1$ the vertebral levels $V_2$ and $V_3$ of the spinal fixation rods 450. The IPG is shown placed below the 3 sets of leads (L) that are routed and placed in therapeutic proximity to the targeted DRG's at the identified spinal levels. The leads (L) are routed along the sides of the spinal cord and are shown as not crossing the midline, though alternate placing of the IPG may result in lead(s) (L) crossing the midline as discussed above.

It will be apparent now to the skilled artisan that alternative embodiments may be provided with identified spinal level(s) resulting in leads L and related electrode(s) E that are placed one or more spinal levels above the identified vertebral levels. Similarly, an alternative may comprise identified spinal level(s) resulting in leads L and related electrode(s) E that are placed one or more identified spinal levels below the identified vertebral levels. Consequently, it will be understood that embodiments may comprise identified spinal level(s) that result in leads (L) and related electrode(s) E that are placed one or more identified spinal levels above and one or more identified spinal levels below the identified vertebral levels. All of these alternatives may also comprise identified spinal levels with related leads (L) and electrode(s) E that are placed within the identified vertebral levels.

FIG. 6 and all alternatives described herein are achieved using an open-access surgical incision that exposes the subject portion of the spinal column, providing the surgeon with physical and visual access to the relevant vertebrae (V).

Figure 7:
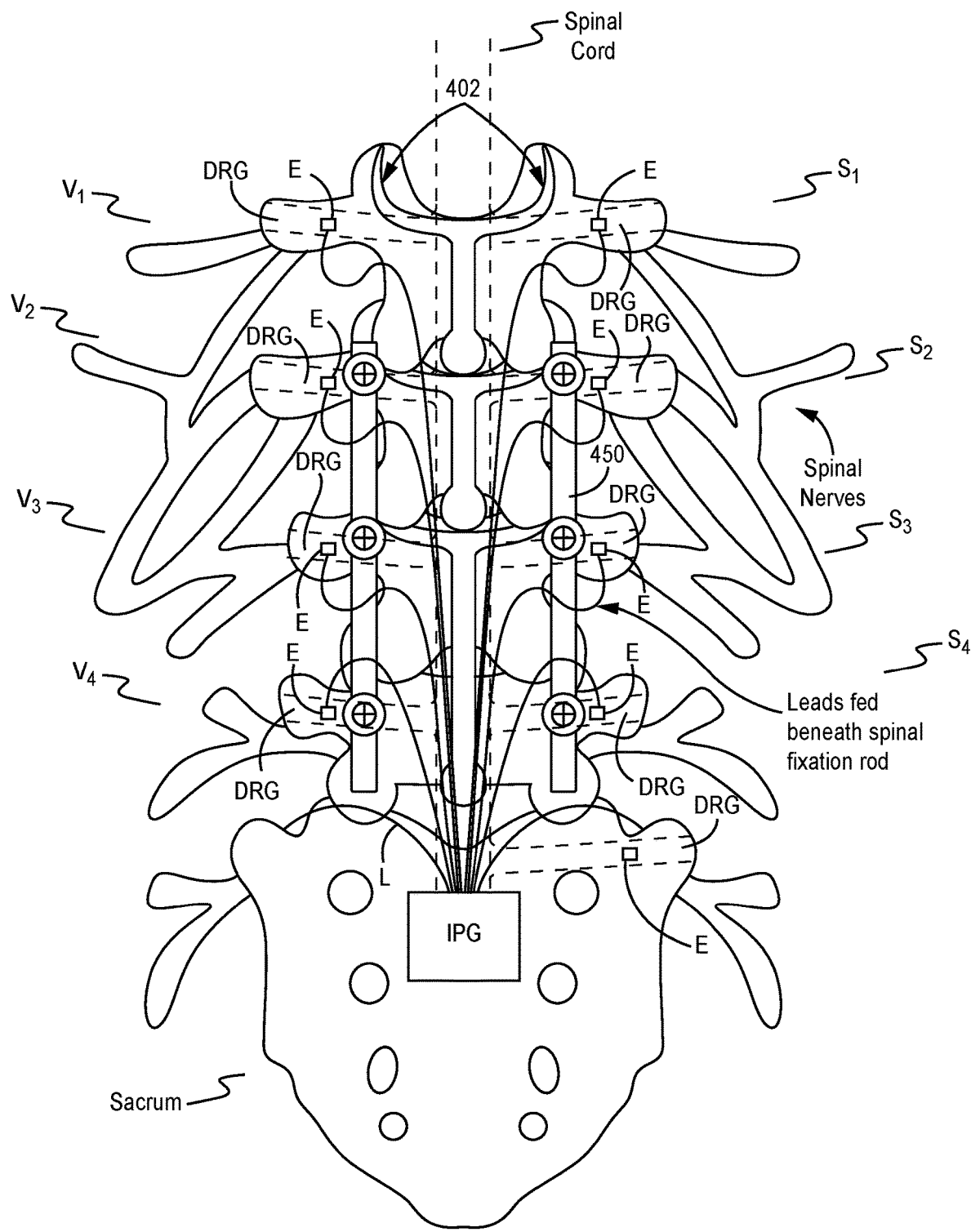
FIG. 7 is a view of an embodiment of the present invention.

FIG. 7 is similar to the previously described illustrations in FIGS. 5 and 6. In this case, however, the spinal treatment site comprises a multi-level spinal fixation device comprising a rod (450) and three pedicle screws (452) securing each rod (450) to vertebrae at the identified vertebral levels $V_2$, $V_3$ and $V_4$ and neuromodulation leads placed at identified spinal levels $S_1$-$S_4$ and another lead in therapeutic proximity to the DRG's at the patient's sacrum as shown. Thus, this embodiment comprises leads (L) with related electrode(s) (E) placed one spinal level above and one spinal level below the vertebral levels of the spinal fixation device. In addition, leads (L) and related electrode(s) (E) are routed and placed at spinal levels corresponding with the identified vertebral levels for the spinal fixation device. As with previously described embodiments, the electrode(s) (E) are placed in therapeutic proximity with a dorsal root ganglion (DRG) and the procedure is executed using an open-access surgical incision that allows visual and physical access to the surgical site.

Figure 8:
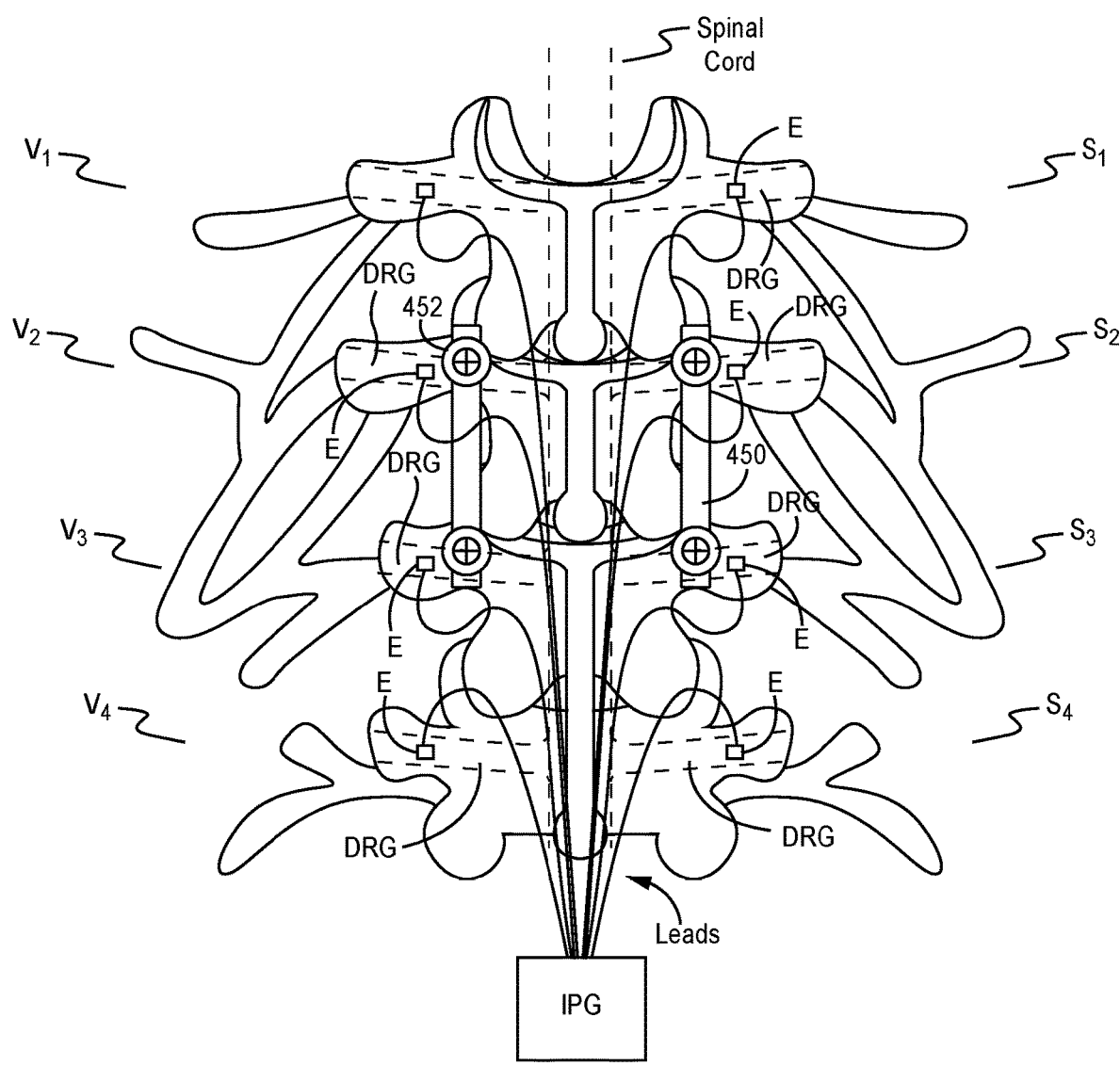
FIG. 8 is a view of an embodiment of the present invention.

FIG. 8 is an illustration of a spinal treatment site comprising a spinal fixation device comprising fixation rods (450) with pedicle screws (452) securing each rod (450) to vertebral levels $V_2$ and $V_3$ and a neuromodulation device comprising 4 sets of bilateral leads (L) with associated electrode(s) (E) placed at spinal levels $S_1$-$S_4$. Accordingly, one pair of bilaterally placed leads (L) and electrode(s) (E) is placed one spinal level above and another pair placed one spinal levels below the vertebral levels $V_2$, $V_3$ of the spinal fixation device. Though not shown, the neuromodulation lead (1) could also be placed two or more levels above and/or two or more levels below the spinal levels of the spinal fixation device's rods 450 and screws 452. In this embodiment, additional neurostimulation leads are shown placed bilaterally at the spinal levels $S_2$ and $S_3$ corresponding to the spinal fixation device. In other respects, FIG. 8 is the same as the system shown in FIG. 6 and described in connection therewith, including placement of the IPG, open access visualization of the surgical site and placement of the lead(s) (L) and associated electrode(s) (E) in therapeutic proximity of the targeted DRG.

FIG. 9A is an illustration of a spinal treatment site including a spinal fixation device comprising rods (450) spanning 4 identified vertebral levels $V_1$-$V_4$ and a neuromodulation device comprising an IPG with leads (L) extending transverse to the spinal cord and midline of the spinal column. The neuromodulation leads (L) have a proximal segment extending in a single sided, unilateral manner with respect to the spinal cord from below the at least some of the targeted DRG's in combination with a distal portion of the neuromodulation lead routed for placement in therapeutic proximity with or to the corresponding dorsal root ganglia target.

In this embodiment, the IPG is placed to one side, or may be external to the patient's body. As shown, this configuration and embodiment comprising placement of the IPG to one side of the spinal cord and/or midline of the spinal column, whether placed internally or externally, results in at least some of the leads (L) being routed across the midline of the spinal column to place the related electrode(s) (E) in therapeutic proximity with the targeted DRG's. Further, as with all described embodiments, the illustrated system is achieved using an open-access surgical incision that enables visual and physical access of the targeted surgical site.

Figure 9B:
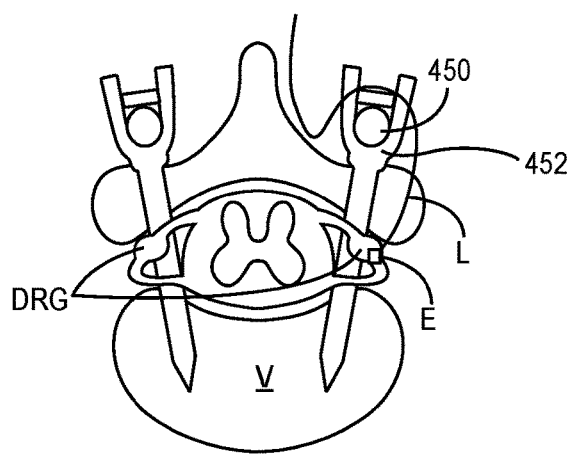
FIG. 9B is a top cross-sectional view of an embodiment of the present invention.

FIG. 9B is a top cross section of a vertebra (V) and related routing of a lead (L) and placement of electrode(s) (E) from FIG. 9A. Thus, a spinal fixation device comprising a fixation rod (450) and neuromodulation device with a lead placed in therapeutic proximity to the dorsal root ganglia target. The illustrated configuration is representative of, and may be generally applied to, all embodiments described herein.

Figure 10A:
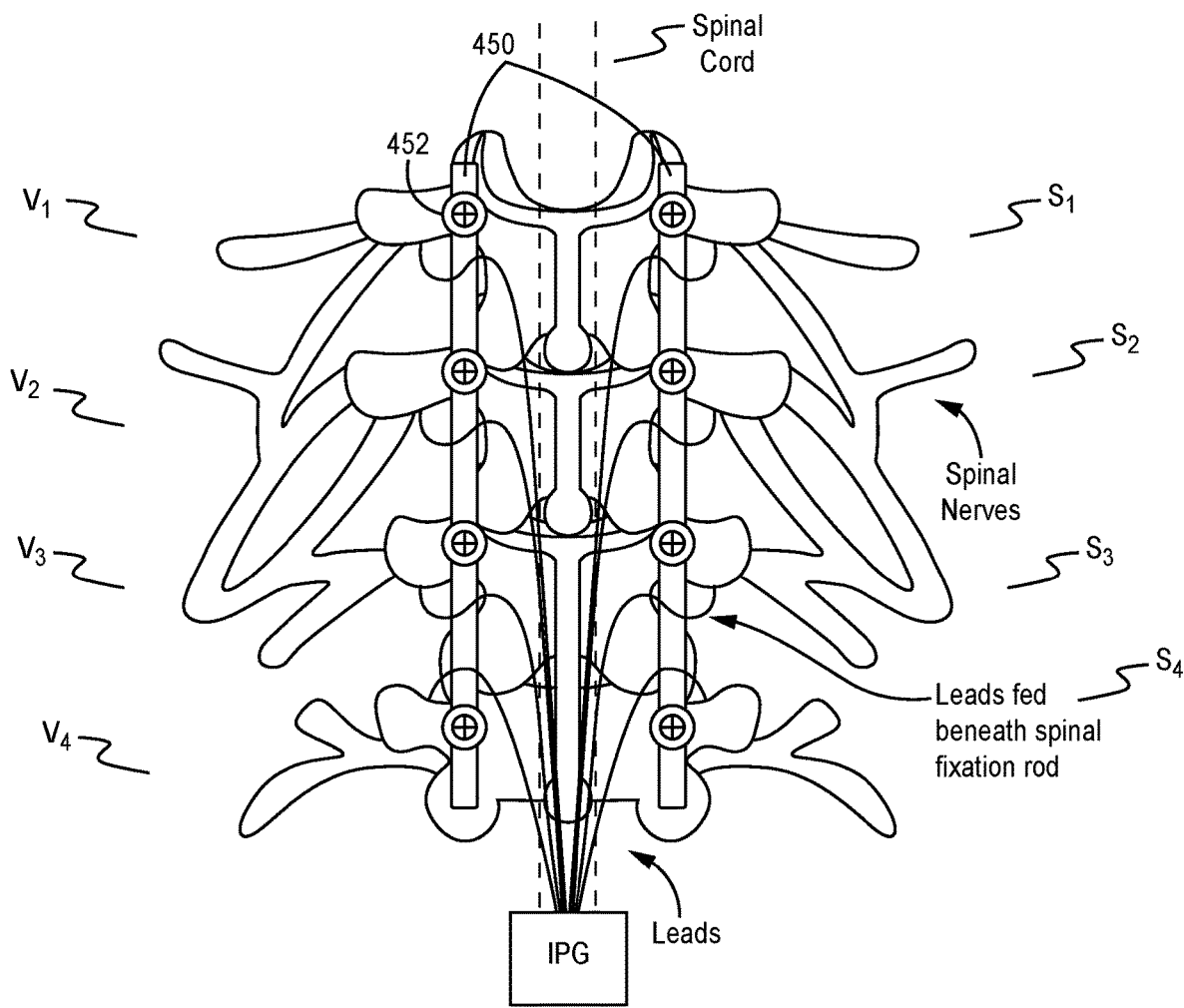
FIG. 10A is a view of an embodiment of the present invention.

FIG. 10A is an illustration of a spinal treatment site including a spinal fixation device comprising a pair of fixation rods (450) and related pedicle screws (452) and neuromodulation device comprising an IPG in operative electrical connection with leads (L) extending transforaminally to the corresponding dorsal root ganglia DRG wherein electrode(s) (E) are placed in therapeutic proximity therewith. FIGS. 4-10A show various arrangements of spinal fixation devices and neurostimulation lead placement combinations. In more detail, the leads (L) may take various lead placement paths in order to achieve or maintain therapeutic proximity to a target dorsal root ganglia. As shown in FIG. 10A, for example, the multi-level spinal fixation device is illustrated with a pedicle screw (452) attached at each identified vertebral level, $V_1$-$V_4$ in this case. The neurostimulation lead (L) pathways may include a segment of the neurostimulation lead (L) extending between an adjacent pair of pedicle screws (452) on the same fixation rod (450), and the neurostimulation lead (L) may further extend or route underneath the corresponding rod (450) before looping around the corresponding target dorsal root ganglia. The distal segment of the neurostimulation lead (L) comprising associated electrode(s) (E) may then contact or otherwise be placed in therapeutic proximity to the corresponding target dorsal root ganglia DRG by looping or curving around the target dorsal root ganglia DRG. Placement pathways in accordance with the present invention may include a segment of a lead L extending between a pair of adjacent pedicle screws (452) positioned at a target vertebral level and a distal segment of the neurostimulation lead (L) extending to a spinal level at the same level as the vertebral level or one spinal level above the target vertebral level or two levels above the target vertebral level. Additional placement pathways in accordance with the present invention include a distal segment of the neuromodulation lead (L) being placed in a retrograde approach to the corresponding target dorsal root ganglia DRG such that it is looped over the target dorsal root ganglia DRG, such a placement pathway may extend from a segment of the neuromodulation lead L originating from a spinal level above or a spinal level below the target dorsal root ganglia DRG.

This open-access surgical incision described herein enables full visual and physical access to the system described herein and the targeted DRG, making the described routing of leads (L) and placement of associated electrode(s) (E) possible.

Figure 10B:
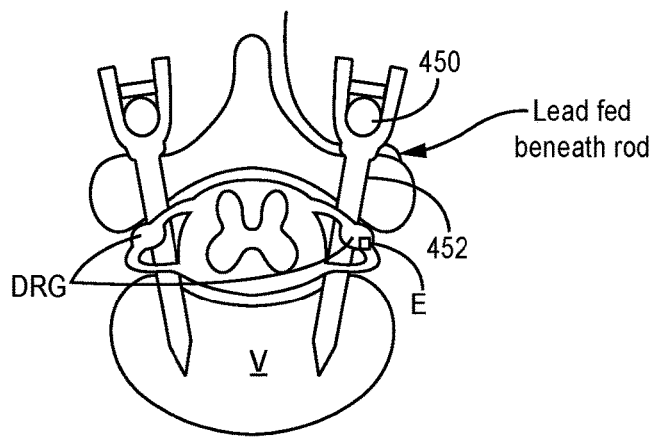
FIG. 10B is a top cross-sectional view of an embodiment of the present invention.

FIG. 10B is a top cross section of a spinal treatment site from FIG. 10A and similar to that of FIG. 9B, including a spinal fixation device comprising fixation rods (450) and pedicle screws (452) and a lead (L) with associated electrode(s) (E) placed in therapeutic proximity to the dorsal root ganglia DRG, wherein the lead (L) is routed beneath the fixation rod (450).

In some embodiments described herein, it is contemplated that the implantable pulse generator (IPG) may be placed within the spinal treatment site, as described above, or may be placed remotely from the spinal treatment site such as in the flank or buttocks area of the patient with neuromodulation leads (L), and lead extensions if necessary, extending from the spinal treatment site to the remote location of the implantable pulse generator (IPG).

Alternatively, it is contemplated that a trial stimulation procedure may be performed where the neurostimulation leads (L) may be placed in therapeutic proximity with at least one target DRG as described supra, and wherein the placed leads (L) may extend from the treatment site in any of various placement arrangements in accordance with the present invention, including but not limited to those discussed above or below, and wherein a proximal end of the leads (L) may extend external to the patient's body such that an externally positioned pulse generator (EPG) may be electrically operatively coupled to the leads (L) for a trial neuromodulation procedure prior to a full implant of the implantable pulse generator.

Embodiments of an IPG placement are illustrated in FIGS. 11 and 12. FIG. 11 is an illustration of an IPG placement site in a flank of a patient. FIG. 12 is an illustration of an IPG placement site at the spinal treatment site. FIG. 13 is an illustration of an external pulse generator (EPG) coupled to neurostimulation leads L extending external to the patient and electrically coupled with the EPG, and wherein a distal segment of the leads (L) are routed within the patient's body and associated electrode(s) (E) placed proximal to the target DRG.

Figure 14:
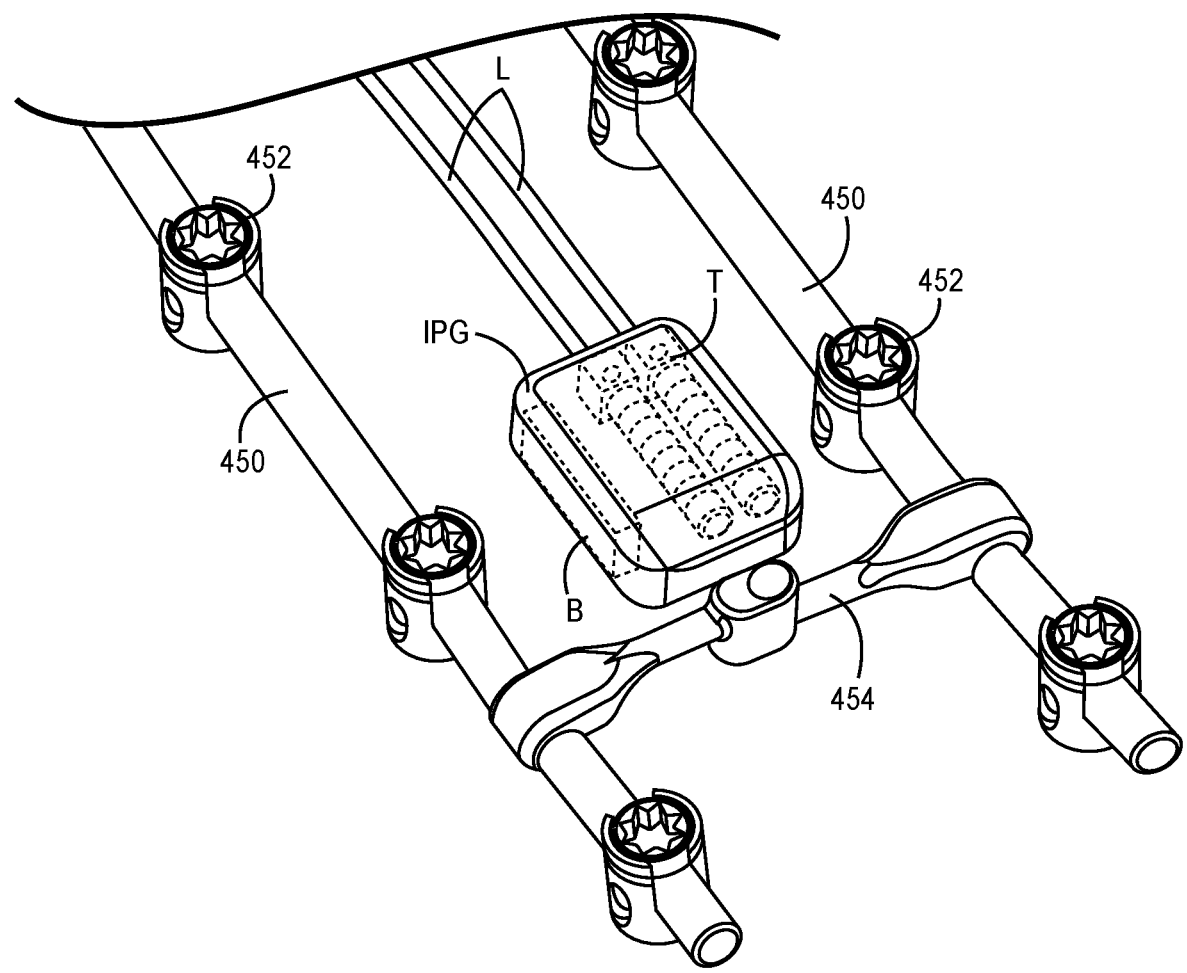
FIG. 14 is a perspective view of an embodiment of the present invention.
Figure 15:
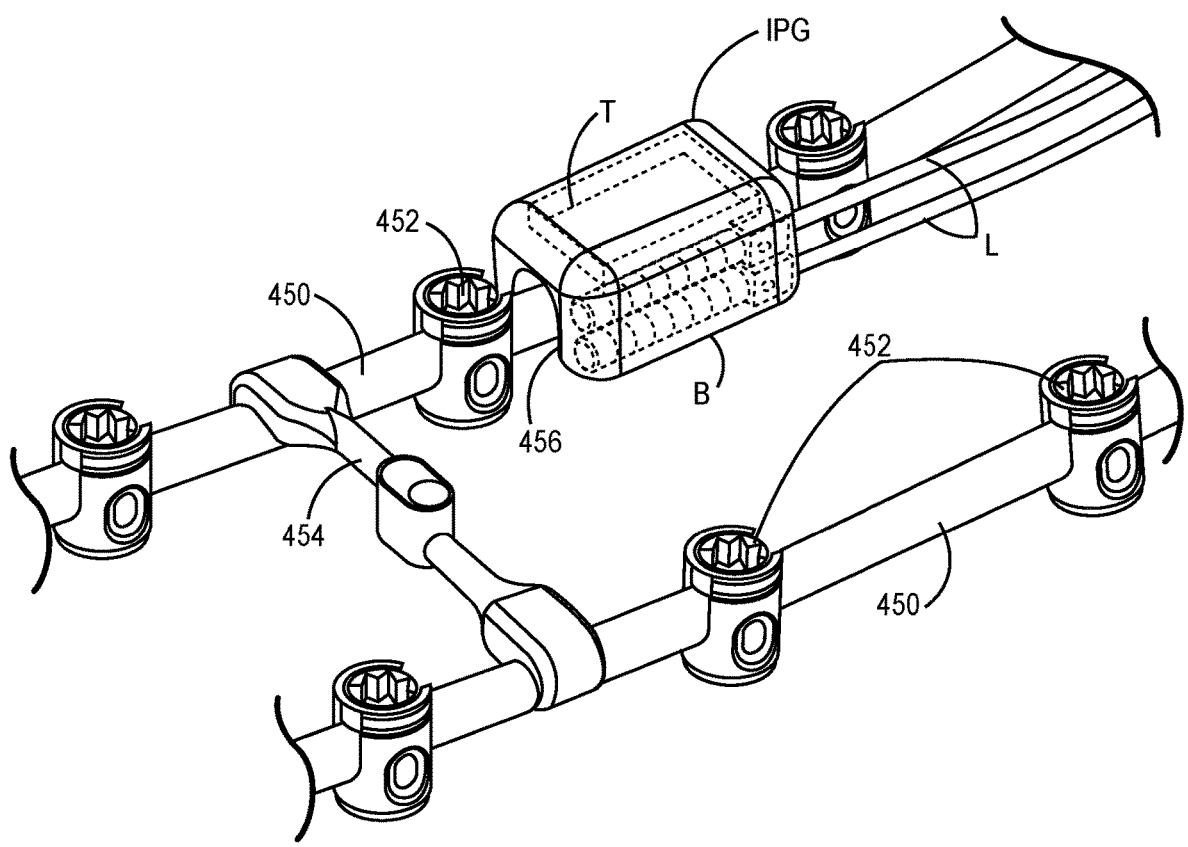
FIG. 15 is a perspective view of an embodiment of the present invention.
Figure 16:
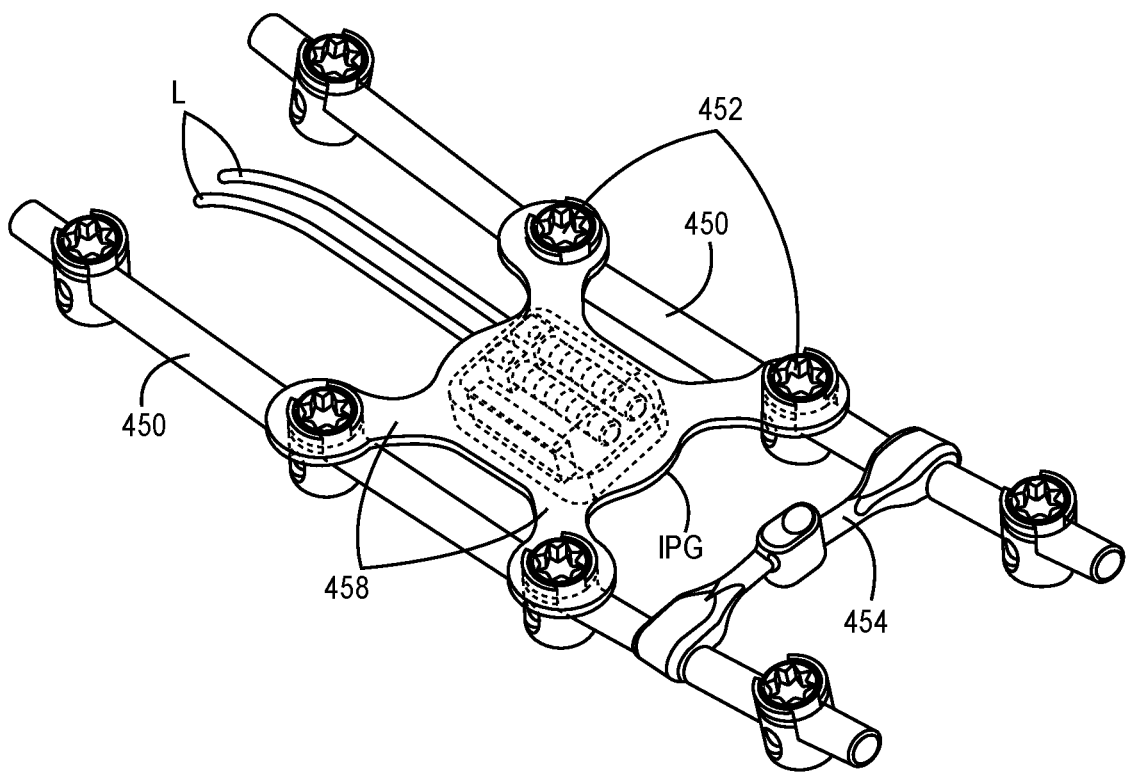
FIG. 16 is a perspective view of an embodiment of the present invention.

FIGS. 14-16 are illustrations of embodiments of an implantable pulse generator at a spinal treatment site.

FIG. 14 is an illustration of an implantable pulse generator (IPG) positioned at a spinal treatment site wherein a portion of the vertebral bone at the spinal treatment site has been removed to create space to place the IPG therein or there along. The IPG has a top (T) and bottom side (B), each having a length and a width. The top and bottom sides (T, B) are generally flat and rectangular in shape, and may include rounded corners, the top and bottom sides are spaced in a generally parallel relationship to each other. The IPG further comprises connecting sides extending between the top and bottom sides, the connecting sides having a vertical dimension corresponding to the distance between top and bottom sides and the vertical dimension being smaller than either the length or width of the top and bottom sides. The IPG is dimensioned to fit within the spinal treatment site with a low vertical profile and to provide a length and width designed to fit within the cleared out bone portion of the spinal treatment site. Thus, in some embodiments, the IPG may be placed between the fixation rods (450) as shown. In this embodiment, the IPG is thus placed within the identified vertebral levels stabilized by the fixation rods (450). A spanning rod (454) is shown that spans the two fixation rods (450). In some embodiments, the IPG may be affixed to one or both fixation rods (450) and/or the spanning rod (454).

In other embodiments, the IPG may be placed in a cleared-out bone portion that is at a vertebral level that is lower, or higher, than the identified vertebral levels.

FIG. 15 is an illustration of another embodiment of an IPG and placement thereof, wherein the IPG is connected to a spinal fixation device comprising two fixation rods (450) and an optional spanning rod (454). The IPG comprises a top (T) and bottom (B) side, each side having a length and a width. The top side (T) may be generally flat and rectangular in shape, and may include rounded corners. The bottom side (B) may comprise a periphery that extends in parallel to the top side with the exception of a rod fixation element (456) formed therein that enables the IPG to be fixated to one of the fixation rods (450). The IPG further having connecting sides extending between the top and bottom sides T,B, the connecting sides having a vertical dimension corresponding to the distance between top and bottom sides and the vertical dimension being smaller than either the length or width of the top and bottom sides. In this embodiment, the bottom side (B) has a rod fixation element (456) defined by a curved receptacle portion extending along a length of the bottom side, the curved receptacle portion being configured to engage a corresponding curved surface of the rod of the spinal fixation device in order to maintain placement and position of the implantable pulse generator when implanted at the spinal treatment site. Generally, the shape of the rod fixation element (456) may be complementary to the shape of the relevant fixation rod (450) to which it will be affixed. This complementary shaping may be generally circular, elliptical, curvilinear or any other complementary geometrical shaping that enables the rod fixation element (456) to fit along the fixation rod (450). Thus, the placement of the IPG in this embodiment is within the identified vertebral levels.

FIG. 16 is an illustration of another IPG embodiment, and placement thereof, connected to a spinal fixation device comprising fixation rods (450) and pedicle screws (452) with an optional spanning rod (454), all as described supra. The implantable pulse generator has a top and bottom side, each having a length and a width. The top and bottom sides are generally flat and rectangular in shape, and may include rounded corners, the top and bottom sides are spaced in a generally parallel relationship to each other. The implantable pulse generator further having connecting sides extending between the top and bottom sides, the connecting sides having a vertical dimension corresponding to the distance between top and bottom sides and the vertical dimension being smaller than either the length or width of the top and bottom sides. The implantable pulse generator further includes one or more rod fixation extension arms (458) extending from at least one corner of at least a top or bottom side of the implantable pulse generator. As shown in FIG. 16, a rod fixation extension arm (458) extends from each corner of the IPG to connect to a fixation rod (450), preferably secured by interaction with a pedicle screw (452) in a generally X-shaped arrangement. The rod fixation extension arm (458) may be affixed or coupled to the corresponding portion of the rod (450) of the spinal fixation device by fitting over a corresponding pedicle screw (452) segment at the corresponding coupling location such that each of the four rod extension arms (458) couples to, or is affixed by, a separate pedicle screw (452) in order to maintain the placement of the IPG at the spinal treatment site.

Alternatively, one or more rod fixation extension arms (458) may extend from the IPG to connect with the fixation rod(s) (450) and/or pedicle screw(s) (452). Still more alternatively, one or more rod fixation extension arms (458) may extend from the IPG to connect with the spanning rod (454) when spanning rod (454) is present.

Thus, the IPG of FIG. 16 will be placed within the identified vertebral levels and may be secured and used in combination with the bone-clearing placement embodiment of FIG. 14 to minimize the vertical rise of the placed IPG.

The description of the invention and is as set forth herein is illustrative and is not intended to limit the scope of the invention. Features of various embodiments may be combined with other embodiments within the contemplation of this invention. Variations and modifications of the embodiments disclosed herein are possible and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A method for treating pain generated by a patient's spinal column having a midline with neuromodulation stimulation, comprising:
   identifying one or more targeted spinal levels for neuromodulation stimulation;
   creating an open access into a resulting spinal treatment site to provide full visual and physical access to at least one dorsal root ganglion at the at least one identified targeted spinal level; and
   placing a neuromodulation system comprising:
      an implantable pulse generator,
      at least one electrical lead in operative electrical communication with the implantable pulse generator and that is routed from the implantable pulse generator to at least one dorsal root ganglion at each of the one or more target spinal levels, and
      at least one electrode disposed at a distal end of the at least one electrical lead, wherein the at least one electrode is placed in therapeutic proximity with each of the at least one dorsal root ganglion at at least one or more target spinal levels;
   closing the open access; and
   delivering a neuromodulation stimulation therapy to the at least one dorsal root ganglion with the neuromodulation system after closing the open access.

2. The method of claim 1, further comprising delivering a neuromodulation stimulation therapy with the neuromodulation system before closing the open access.

3. The method of claim 1 further comprising conducting a spinal procedure after closing the open access.

4. The method of claim 3, wherein the spinal procedure comprises:
   identifying two or more targeted vertebral levels for vertebral stabilization;
   creating an open access into the resulting spinal treatment site to provide full visual and physical access to the identified targeted vertebral levels and the previously placed neuromodulation system;
securing bilaterally spaced fixation rods across the two or more targeted vertebral levels;
closing the open access; and
continuing to deliver neuromodulation stimulation therapy with the neuromodulation system after the open access is closed.

5. The method of claim 4, further comprising delivering neuromodulation stimulation therapy with the neuromodulation system after the spinal procedure is complete and before closing the open access.

6. The method of claim 4, wherein at least routed one electrical lead is disposed beneath a secured fixation rod.

7. The method of claim 4, wherein at least one electrical lead is disposed above a secured fixation rod.

8. The method of claim 4, wherein the placed IPG is positioned between the secured bilaterally spaced fixation rods.

9. The method of claim 8, wherein the placed IPG is secured to at least one of the secured bilaterally spaced fixation rods.

10. The method of claim 4, wherein at least one identified targeted spinal level is located at least one level above the identified targeted vertebral levels.

11. The method of claim 4, wherein at least one identified targeted spinal level is located at least one level below the identified targeted vertebral levels.

12. The method of claim 4, wherein at least one identified targeted spinal level overlaps with the identified targeted vertebral levels.

13. The method of claim 1, further comprising routing at least one electrical lead to cross the midline of the patient's spinal column.

14. The method of claim 1, further comprising identifying the midline of the patient's spinal column, and placing the implantable pulse generator along the midline of the patient's spinal column.

15. The method of claim 14, further comprising routing the at least one electrical lead without crossing the midline of the patient's spinal column.

16. The method of claim 14, further comprising placing the implantable pulse generator below each of the at least one electrodes placed in therapeutic proximity with each of the at least one targeted dorsal root ganglion.

17. The method of claim 14, further comprising placing the implantable pulse generator below at least one of the at least one electrodes placed in therapeutic proximity with each of the at least one targeted dorsal root ganglion.

18. The method of claim 1, further comprising placing the implantable pulse generator on one side of the midline of the spinal column.

19. The method of claim 18, further comprising routing at least one electrical lead to cross the midline of the patient's spinal column.

20. The method of claim 18, further comprising placing the implantable pulse generator below at least one of the at least one electrodes placed in therapeutic proximity with each of the at least one targeted dorsal root ganglion.

21. The method of claim 4, further comprising a spanning rod fixed between the two bilaterally spaced fixation rods.

22. The method of claim 4, further comprising affixing the implantable pulse generator to the spanning rod.

* * * * *